Feb. 22, 1955 E. P. SIMA Plant Pat. 1,354
ROSE PLANT
Filed Jan. 13, 1953
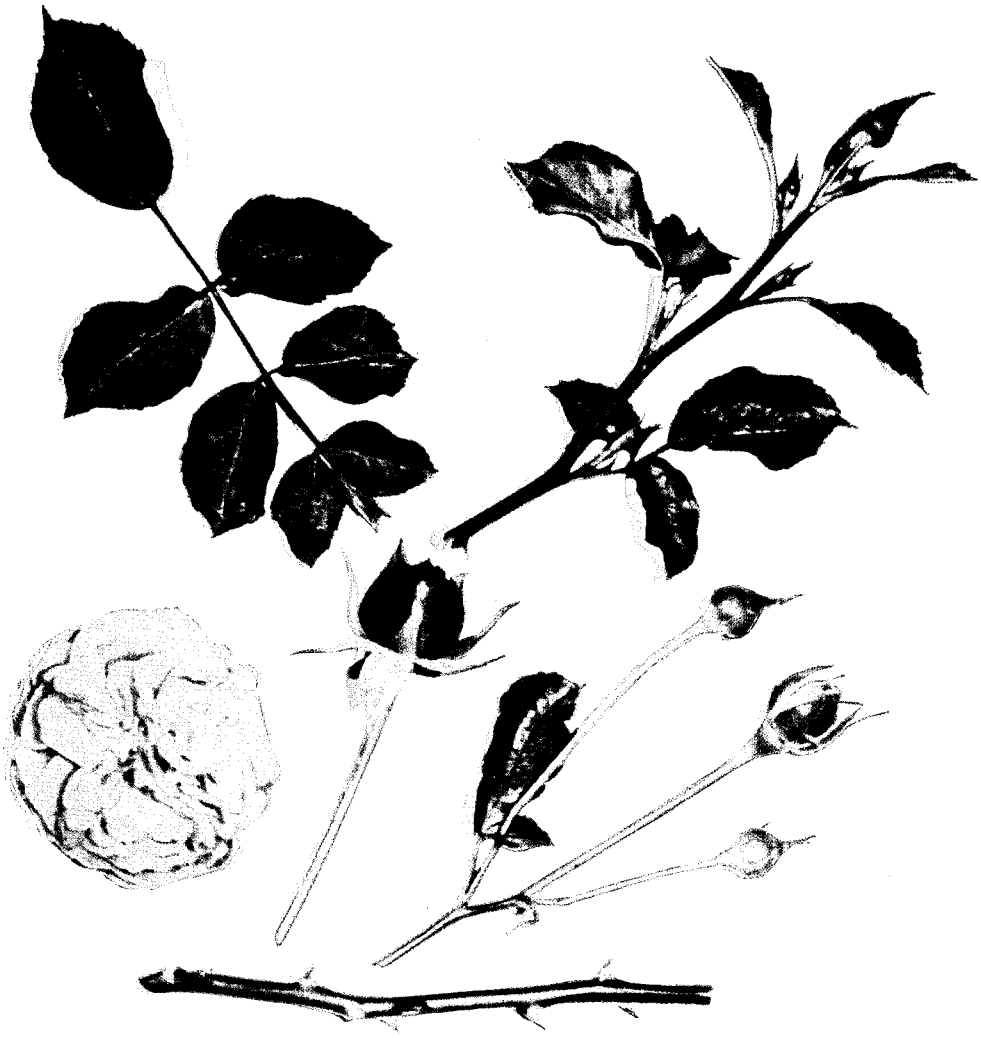
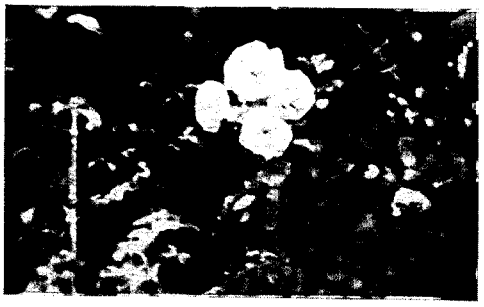
Inventor.
Edward P Sima
By Orville M Kile
Plant pat. Agent United States Patent Office Plant Pat. 1,354

Patented Feb. 22, 1955

1,354

ROSE PLANT

Edward P. Sima, Seattle, Wash.

Application January 13, 1953, Serial No. 331,125

1 Claim. (Cl. 47—61)

The present invention relates to improvements in roses of the type commonly known as climbing roses, in which the main stalks acquire considerable length and when given means of support, "climb" and branch out progressively upward and outward in various directions.

My invention is the result of a definite effort through many breeding experiments conducted by me with various types and varieties of roses, with the purpose in mind of satisfying the desire for a new climbing type rose variety that would possess: (1) an everblooming habit, (2) definite resistance to fungous diseases, (3) immunity to mildew, (4) ample vigor and hardiness, (5) abundant production of flowers throughout the growing season, (6) clusters of pleasingly fragrant, floribunda-type blooms in the red color range, (7) blooms of enduring quality, both on the plant and as cut flowers, and (8) superior bloom resistance to sunburn, discoloration, and adverse weather conditions.

From a number of rose seedlings derived from crossing the well-known variety "New Dawn" (Plant Pat. No. 1) with the variety "Red Ripples" (unpatented), there was selected one outstanding seedling of climbing habit and other desirable breeding characteristics. This seedling was subsequently cross-bred with the pollen of "Red Ripples" and one of the resulting seedlings of that cross is my present invention, in which is found a satisfactory combination of the foregoing desirable qualities.

Asexual reproduction of this new variety, through several succeeding generations by budding, show the distinguishing characteristics of the new variety to be well established.

Both the breeding experiments and the asexual reproduction of my new variety were carried on by me in my garden and backyard greenhouse in Seattle.

The accompanying color illustration shows specimens of the flower at various stages of development, together with portions of the foliage and wood at various stages of maturity—all in full color and as true to nature as it was possible for the artist to depict them.

The color inset illustrates the climbing habit of this new variety, as well as showing an average flowering cluster of five blooms in which the uppermost bloom has been opened for ten days; the other three blooms from right to left having been opened 3, 5, and 7 days respectively; and the fifth bloom in the cluster just starting to open. The color inset further shows the central section of a main stalk trained horizontally, which grew to a length of 8 feet and 3 inches from a budding eye inserted into a rootstock on July 4th and which bore a terminal cluster of blooms on November 15th of the same year. This stalk was photographed on August 15th the following year, at which time it had produced 23 blooming laterals, many of which had bloomed a second time from sub-lateral branchings most of which had already been cut off for propagating buds at the time the photograph was taken.

Following is a detailed description of my new variety, color terminology being in accordance with both "Ridgway's Color Standards and Nomenclature" and "Wilson's Horticultural Colour Chart," as indicated by plate numbers.

THE PLANT

Form and classification:

*Commercial.*—Everblooming climber (floribunda type).

*Botanical.*—Hybrid wichuraiana.

Growth: Vigorous; branching but not rampant; suitable as pillar rose and for fence decoration.

Propagation: Although most of the reproduction has been done by means of budding in order to conserve propagation material, the variety roots readily by means of cuttings.

Foliage:

*Type.*—Five to seven leaflets.

*Quantity.*—Abundant.

*Size.*—Medium to large.

*Color.*—New foliage: upper surface Spinach Green (Pl. 0960/1, p. 187), veiled with Oxblood Red (Pl. 00823/3, p. 191); under surface Spinach Green (Pl. 0960/3, p. 187), shaded with Oxblood Red (Pl. 00823, p. 191)—Horticultural Colour Chart.

*Shape.*—Oval, pointed.

*Texture.*—Leathery; glossy; smooth on upper surface. Under surface rough. Ribs and veins prominent.

*Edge.*—Serrated with single, large, irregular serrations.

*Stipules.*—Normal length and width. Points average, turning out at an angle of approximately 45 degrees. Bearded.

*Leaf stem or rachis.*—Grooved above. Under side with few prickles. Dark Cress Green (Pl. XXXI), washed with Hay's Maroon (Pl. XIII) near the axis. (Ridgway.)

Disease resistance: In testing this new variety it has never contracted blackspot or mildew under the conditions grown in the State of Washington, although mildew is found on most rose varieties here in late summer and fall.

Blooming habit: Very prolific bloomer.

Blooming season: Continuous bloomer during growing season; normally from the end of May until stopped by frosts, in this climate.

Wood: New wood—bark smooth. Color Oxblood Red (Pl. I) washed with Light Cress Green (Pl. XXXI). Branches varying from Dark Cress Green (Pl. XXXI) to Cress Green (Pl. XXXI), shaded with Oxblood Red (Pl. I) in varying tones depending on shade and exposure to the sun. (Ridgway.)

Thorns:

*Quantity.*—On main stalks from base and on laterals from stalk, ordinary.

*Form.*—Broad base; medium length; hooked downward.

*Color when young.*—Oxblood Red (Pl. I, Ridgway); transparent.

*Position.*—Irregularly spaced; occasionally appearing in pairs.

*Prickles and short spines.*—None on main stalks and on laterals.

THE FLOWER

Bud:

*Size.*—Small. Approximately ¾ inch in length.

*Form.*—Globular-pointed, with sepals extending about ¼ inch beyond the tip of bud before the calyx breaks. Not affected by hot or wet weather.

*Color.*—When sepals first divide, color is near Chrysanthemum Crimson (Pl. 824, p. 169); when petals begin to unfurl, Cardinal Red (Pl. 822/1, p. 168); when half-blown, inside of petals, Currant Red (Pl. 821/1, p. 167); reverse of petals, near Tyrian Rose (Pl. 24, p. 24). (Horticultural Colour Chart.)

*Sepals.*—Smooth-edged, with normal branching. Reflex when petals begin to unfurl.

*Calyx.*—Small; smooth; funnel-shaped; no odor when rubbed.

*Peduncle.*—Smooth; erect; well-proportioned, medium length (2 to 3 inches). Color near Parrot Green (Pl. VI), with varying shadings of Mahogany Red (Pl. II) superimposed on young peduncles and on surfaces exposed to the sun. (Ridgway.)

*Opening.*—Bud opens up well and is not affected by adverse weather conditions.

Bloom:

*Size.*—Medium, averaging 2 to 2½ inches in diameter when fully open.

*Borne.*—In loose clusters, flat or slightly pyramidal. Normally five blooms in a cluster although sometimes up to eight and occasionally borne singly.

*Form.*—Cupped, with flat center when first opened. After second or third day as flower develops, the outer petals assume a horizontal position approximately at right angles to the peduncle. The petals are progressively shorter toward the center of the bloom, thereby forming a rosette-shaped flower of approximately 1 inch depth, which form is retained. Petals do not quill or reflex. Petaloids are few.

*Petalage.*—Very double, normal conditions producing 60 to 70 petals.

*Color.*—Center of open flower, Carmine (Pl. I), washed with Scarlet Red (Pl. I). Outer petals, Carmine, Pl. I), washed with Tyrian Rose (Pl. XII). Inside of petals, near Tyrian Rose (Pl. XII). Reverse of petals, Rose Color (Pl. XII), tinted with Tyrian Pink (Pl. XII). Aiglet, near Seafoam Green (Po. XXXI). (Ridgway.) General tonality from a distance, Rose Red (Pl. 724, p. 158), and with a definite luminous quality. Discoloration—general tonality at end of first day, Rose Red (Pl. 724, p. 158), tinted with Tyrian Rose (Pl. 24/1, p. 24); second and third days, Rose Red (Pl. 724, p. 158), tinted with Tyrian Rose (Pl. 24/1, p. 24). (Horticultural Colour Chart.) No variegations.

*Flower stems.*—Long; normal; ample strength.

*Fragrance.*—Strong "Sweet Briar" perfume, gradually disappearing from old blooms.

Petals:

*Form.*—Round. Outer petals wavy. Central petals narrower and ruffled.

*Texture.*—Thick to leathery.

*Arrangement.*—Imbricated.

*Appearance.*—Silky. Slightly prominent ribs radiate from aiglet.

*Lasting qualities.*—On the plant, last very long time—during summer, ten days to two weeks; during cool autumn weather, three weeks; during late October and November, blooms have remained on the plant in presentable condition for a period of four weeks. As a cut flower the lasting qualities are also excellent.

*Persistence.*—Petals drop off cleanly.

Reproductive organs:

*Pistils.*—Bunched in center of flower.

Styles—Columnar; uneven lengths, averaging approximately ⅜ inch; slender; near Sap Green (Pl. 62/3, p. 62).

Stigmas—near Chartreuse Green (Pl. 663/3, p. 90).

*Stamens.*—Few; surrounding pistils, and mixed with petaloids.

Anthers—medium size; Buttercup Yellow (Pl. 5/3, p. 5).

Filaments—irregular lengths; short—⅛ to ¼ inch long; mostly with anthers; near Saffron Yellow (Pl. 7/3, p. 7).

Pollen—Saffron yellow (Pl. 7, p. 7). (Horticultural Colour Chart.)

*Ovaries.*—All enclosed in calyx.

Fruit:

*Form.*—Round; slightly depressed top; seeds fully enclosed.

*Aspect.*—Smooth.

*Color.*—At maturity, Capsicum Red (Pl. 715, p. 92). (Horticultural Colour Chart.)

*Sepals.*—Falling soon; moderately long; recurved.

*Occurrence.*—This variety rarely sets hips under usual outdoor growing conditions. Shortly after the flower drops off, the peduncle with calyx also drops off cleanly. However, hips will set seeds when cross-pollenized with certain varieties.

COMPARISON

The physical plant characteristics of this new variety resemble those of the variety "New Dawn" (Pl. Pat. No. 1) as applying only to wood growth, branching habit and overblooming habit, substantially as described by lines 23 to 46 of Plant Patent No. 1. But the flower of this new variety is distinctly different as to form, color, fragrance, endurance, and substance. Furthermore, the entire plant structure of this new variety has been entirely immune from mildew under the most adverse conditions, and this is not true of "New Dawn" which under certain conditions is susceptible to mildew.

The flower of the new variety compares with that of its pollen parent "Red Ripples," as follows:

The new variety has three to four times as many petals, so that when both are at full-open stage the new variety displays a full, rounded center, while the center of "Red Ripples" is approximately flat and open.

The outer two or three rows of petals of both varieties are very similar in their shape and wavy aspect of the open flower. However, when viewed from a distance, the full-center bloom of the new variety portrays a distinctive alluring luminosity not persent in the coloring of "Red Ripples." Nor is this quality to be found in any other open-center rose of the red color range, so far as I know.

The petal substance of the new variety and of "Red Ripples" is substantially the same.

The fragrance of the new variety is distinctly different and stronger.

The genital organs of "Red Ripples" are more developed and conspicuous and commonly set fruit readily, whereas the new variety does not set fruit readily.

Having thus disclosed my invention, I claim:

The new and distinct variety of climbing rose plant, substantially as herein described and illustrated, differing from any other commercial rose variety known to me because of its particular combination of numerous desirable qualities, characterized particularly by its ample vigor and hardiness; its resistance to mildew and blackspot where tested; its free-branching habit of plant growth; its abundant glossy foliage; and its overblooming habit with plentiful production of clusters of fragrant, floribunda-type red flowers possessing exceptional enduring qualities as well as superior resistance to sunburn, discoloration and adverse weather conditions.

No references cited.